US009809911B2

(12) United States Patent
Peroz

(10) Patent No.: US 9,809,911 B2
(45) Date of Patent: Nov. 7, 2017

(54) DEVICE FOR MOULDING FIBROUS MATERIAL

(75) Inventor: Jacky Peroz, Corbarieu (FR)

(73) Assignee: AUTONEUM MANAGEMENT AG, Winterthur (SE)

(*) Notice: Subject to any disclaimer, the term of this patent is extended or adjusted under 35 U.S.C. 154(b) by 716 days.

(21) Appl. No.: 14/117,490

(22) PCT Filed: May 8, 2012

(86) PCT No.: PCT/EP2012/058446
§ 371 (c)(1),
(2), (4) Date: Apr. 3, 2014

(87) PCT Pub. No.: WO2012/156234
PCT Pub. Date: Nov. 22, 2012

(65) Prior Publication Data
US 2014/0205700 A1  Jul. 24, 2014

(30) Foreign Application Priority Data
May 19, 2011  (EP) .................................. 11166646

(51) Int. Cl.
*D04H 1/00* (2006.01)
*D04H 1/60* (2006.01)
(Continued)

(52) U.S. Cl.
CPC ............. *D04H 1/005* (2013.01); *D04H 1/558* (2013.01); *D04H 1/60* (2013.01); *D04H 1/732* (2013.01);
(Continued)

(58) Field of Classification Search
CPC ...... A61F 2013/15943; A61F 13/15626; A61F 2013/15902
See application file for complete search history.

(56) References Cited

U.S. PATENT DOCUMENTS 2,651,808 A * 9/1953 Burnett ................ A22C 11/108
222/218
2,935,828 A * 5/1960 Mahaffy ................ B29C 51/225
425/388
(Continued)

FOREIGN PATENT DOCUMENTS

CN         1258598 A     7/2000
WO     WO 96/16804     6/1996
(Continued)

OTHER PUBLICATIONS

International Search Report issued by the European Patent Office in corresponding International Application No. PCT/EP2012/058446.

*Primary Examiner* — Matthew Daniels
*Assistant Examiner* — Kimberly A Stewart
(74) *Attorney, Agent, or Firm* — Lewis Brisbois Bisgaard & Smith LLP

(57) ABSTRACT

A device for producing a 3 dimensional shaped consolidated product. The device includes a rotary drum, defined as a rotary conveyor with a peripheral surface extending in circumferential direction with at least one product shaping area in the form of a cavity on said peripheral surface, the peripheral surface is pervious to air at least in the product shaping area, at least one material feed device to feed a base material into the at least one cavity, a vacuum device designed to generate a negative pressure at least in the at least one cavity, whereby the generated suction is directed towards the interior of the rotary conveyor, and whereby downstream of the material feed device at least one consolidating device is located such that at least a part of the filled cavity is subjected to a consolidating treatment whereby the base material at least partly will adhere to neighboring material.

18 Claims, 2 Drawing Sheets

(51) Int. Cl.
  *D04H 1/732* (2012.01)
  *D04H 1/558* (2012.01)
  *D04H 1/76* (2012.01)
  *A61F 13/15* (2006.01)

(52) U.S. Cl.
  CPC .......... *D04H 1/76* (2013.01); *A61F 13/15626* (2013.01); *A61F 2013/15902* (2013.01); *A61F 2013/15943* (2013.01)

(56) References Cited

U.S. PATENT DOCUMENTS

| | | | |
|---|---|---|---|
| 4,212,609 A | * | 7/1980 | Fay .......... A21C 9/04 425/100 |
| 4,874,456 A | * | 10/1989 | Takagi .......... A61F 13/15674 156/301 |
| 5,064,484 A | * | 11/1991 | Craig .......... A61F 13/15626 156/296 |
| 5,081,819 A | * | 1/1992 | Cloud .......... B65B 1/366 425/373 |
| 5,226,991 A | * | 7/1993 | Svaighert .......... A61F 13/15626 156/251 |
| 2002/0012731 A1 | * | 1/2002 | van Esbroeck .......... A21C 11/00 426/512 |
| 2003/0236510 A1 | * | 12/2003 | Yasumura .......... A61F 13/15626 604/367 |
| 2004/0061263 A1 | * | 4/2004 | Daniels .......... A61F 13/15203 264/518 |
| 2005/0220932 A1 | * | 10/2005 | van der Eerden ... A22C 7/0069 426/1 |
| 2008/0111270 A1 | * | 5/2008 | Van Valkenburgh .......... A61F 13/15626 264/113 |

FOREIGN PATENT DOCUMENTS

| | | |
|---|---|---|
| WO | WO 98/30371 | 7/1998 |
| WO | WO 2005/110312 | 11/2005 |
| WO | WO 2007/134812 | 11/2007 |
| WO | WO 2009/043195 | 4/2009 |

* cited by examiner

DEVICE FOR MOULDING FIBROUS MATERIAL

CROSS-REFERENCE TO RELATED APPLICATIONS

This is a U.S. National Phase Application of International Application No. PCT/EP2012/058446, filed May 8, 2012, which claims the benefit of priority to European Patent Application No. 11166646.7, filed May 19, 2011, which is incorporated herein by reference.

TECHNICAL FIELD

The invention relates to a production device for producing three-dimensional shaped fibrous mats for use as or in automotive acoustic trim parts.

BACKGROUND ART

In the automotive industry fiber felt materials are used in a broad range of products for sound insulation for instance in doors, roof lining, the floor area or as inner dash cladding. These products are formed and cut from large felt blanks to fit in the available space. Certain areas of such parts need higher amounts of material to obtain locally higher noise attenuation. In particular, the inner dash situated inside the passenger compartment and covering the wall between the engine bay area and the passenger compartment as well as certain areas of the floor covering have areas of increased fiber density. Felt products can be combined with other materials like mass layer to form a spring mass system or they can be used on their own to function as an acoustic absorbing layer. In all cases they can also be combined with aesthetic or acoustic covering layers, like thin nonwoven, needle punch or tufted carpets. These products need to follow the shape and contour of the area they need to cover as well as need to have fiber free areas for instance for fastening means and to go around appliances in a vehicle.

Fiber-felt products are classically produced from preformed constant density fiber mats containing binder fibers or resins, which are pressed in a heated mould and cut to obtain the desired form and stiffness. A disadvantage of this method is that the grammage of the product depends on the density of the fiber mat and is therefore restricted, either the density of the mat used is too high for most of the surface area moulded or areas with a higher grammage can only be achieved by additionally supplying the material by hand. This is time consuming and/or very expensive. Furthermore because the fiber mats are delivered as a roll good or as pre-cut mats the production process is bound to render a lot of scrap material. Another disadvantage of the use of preformed fiber mats is that they easily tear or break when they are pressed in more extreme contoured moulds. As the products can only be cut after a binding step, the scraps after cutting are of mixed heat set material that cannot be used anymore in the process. The material is due to its mixed nature difficult to recycle. This is a real problem for the automotive industry.

WO 2007/134812 describes an apparatus and a method for manufacturing non-woven products. The apparatus comprises a rotating drum on which a material shaping area in the form of a mould cavity is provided. The mould cavity corresponds to the negative form of the wanted product. Within the drum, vacuum means are provided in order to suck air through openings in the wall of the mould cavity. Fiber material is fed to the mould cavity by means of a fiber feed device. The fibers and hence the wanted product formed thereof are held in the mould by a negative pressure applied to the mould cavity, i.e. the material is held in the mould by the suction airflow while the drum is rotating and is carrying the mould cavity to a transfer device at which the formed material is demoulded. The vacuum compacts the fibers enough to keep a certain shape, however upon demoulding the shape will flatten out as there is no real binding between the fibers. This effect can worsen when synthetic fibers are used alone or in a blend as they are smoother and slide easier.

After the de-moulding step the formed unbonded material can be supplied to a further mould, particularly a compression mould or can be directly subjected to a heat treatment in a through hot air oven. In the further moulding step a non-woven product with a final shape is formed from the formed material by applying heat and pressure.

The described method and apparatus has the advantage that at least the formed material can be manufactured in a continuous manner by means of continuous rotation of the drum. However, as the formed material often consists of unbonded fibrous material, the handling of the formed material during and after the de-moulding step until it is heat set is delicate. During this process period the formed material can likely lose its wanted shape or even be disintegrated. In particularly fibre free areas will fill up again during demoulding. Furthermore the instable structure of the formed material is difficult to put in a follow-up mould precisely as a correction after lay down is not possible anymore. Slight offsets can occur and the product finally produced is prone to rejection at quality control, for not fitting the 3D shape asked for.

SUMMARY OF INVENTION

It is therefore an object of the invention to further develop the apparatus of the state of the art in particularly overcoming the disadvantages.

The device described herein achieves this object. The device according to the appended claims comprises a rotary drum, defined as a rotary conveyor with a peripheral surface extending in circumferential direction with at least one product shaping area in the form of a cavity being on said peripheral surface, the peripheral surface is pervious to air at least in the product shaping area, at least one material feed device to feed a base material into the at least one cavity a vacuum device designed to generate a negative pressure at least in the at least one cavity, whereby the generated suction is directed towards the interior of the rotary conveyor;

characterized in that downstream of the fiber feed device at least one consolidating device is such that at least a part of the filled cavity is subjected to a consolidating treatment such that the base material at least partially will adhere to neighbouring material.

The product obtained by the device according to the invention is a consolidated 3-dimensional shaped part made of base material, like fibers, and which can be used as trim part directly for a vehicle or can be further processed, for instance by adding additional layers or by further forming to material in a second moulding step. Further process steps may include trimming, cutting, punching, laminating, but not necessarily a further shaping step.

The Rotary Drum

The rotary drum is a cylindrical drum with an axis of rotation parallel to the circumferential surface. The rotary drum is surrounded by different processing zones positioned parallel to the circumferential surface of the drum containing the product shaping area(s) (cavity). Preferably the circumferential surface of the drum is in approximately horizontal position and the first processing zone—feeding the base material to the cavities—is located approximately at the high end of the drum to obtain a fiber feeding that is not against gravity. At least a second processing zone is located in rotation direction downstream and contains the consolidation of the base material in the cavity. Eventually a third processing zone—cooling the consolidated material—is located subsequently. Finally a last processing zone to empty the cavity is located after the second or third zone. Preferably this last processing zone is allocated such that the gravity enhances the emptying of the cavity. The axis of rotation of the rotary conveyor preferably lies in a plane, which is arranged essentially perpendicular to the direction of gravitational force. The product shaping area (cavity) preferably extends perpendicular or at least essentially perpendicular to radial lines emanating from the axis of rotation of the rotary conveyor.

The rotary drum contains at least one product shaping area defined as a cavity on its circumferential surface. The product can stretch over the entire circumferential surface in rotary direction or only on part of it. Depending on the size of the products to be produced the size of the product shaping area, as well as the number of such areas on one drum can vary. It is also possible that different product shaping areas are arranged on one drum, to produce different products. It is also possible to have a product shaping area that is endless giving a continuous product, like a mat of fibers or a continuous band.

The depth of the cavity can vary to obtain a preform that is 3 dimensional in form, having an area weight distribution over the width and length of the preform.

At least the cavity is lined with an air pervious material, to let the air stream flow through, but to stop the fibers from passing, such that the cavity is filled up evenly with the base material. If necessary the cavity lining can have a difference in air resistance to increase or decrease the flow of the mixture of air and base material locally. The lining can be made of a single layer or multiple layers, preferably of a metal mesh or fine wire cloth in direct contact with the base material and at the side away from the material a more stronger material like a larger mesh or rough wire, to obtain a stable form for the 3D shape wanted. The surface of the rotary drum is preferably easy replaceable. For instance by a sliding mechanism or by using easy fastening mechanisms to close the surface with the cavities around the circumferential of the rotary drum. Interchangeable surfaces for rotary drums are known in the art.

Underneath at least the pervious areas, a vacuum device designed to generate a negative pressure towards the interior of the rotary conveyor is allocated. The vacuum pressure not only secures the base material during the feeding process but may also draw air through the part in the later processing steps like heating and/or cooling.

The vacuum pressure might be adjustable at the different treatment zones, in particularly a reduction during the heat setting and afterwards the cooling process as well as a reduction to zero during the demoulding process.

The vacuum device is designed to apply a negative pressure on the air-previous product shaping area in order to suck and hold the base material, in the cavity during at least one, several or all process steps. The vacuum device is preferably designed to apply a negative pressure on the product shaping area in the different processing zones. In a preferred embodiment of the invention device for producing the negative pressure is designed such that the different processing zones can be adjusted independent and do not interfere with the other processing zones, optionally even in a processing zone, the vacuum might be adjusted in sub zones to optimise even further.

During the continuous production of the 3 Dimensional moulded heat set fibrous products the rotary drum preferably turns at a continuous speed. The speed might be adjustable depending on the products to be produced. Once the optimum speed is found, the speed can be maintained constant during the continuous production of the parts. If a constant speed is used, all the different treatments, filling of the cavity, heat setting of the material and eventually cooling as well as the demoulding must be adjusted to this one constant speed of the rotary drum.

Feeding Device

In the first processing zone the base material is fed into at least part of the product-shaping cavity using a feeding device whereas the product shaping area is moving continuously, preferably at constant speed, in rotary direction. So it is possible that the product-shaping cavity expands to a larger area than the base material feeding device covers, in such a case the product-shaping cavity will gradually fill up as the cavity moves under the base material feeding device in rotary direction. The base material feeding device is at least covering the largest width of the cavity in the perpendicular direction to the circumferential direction of the drum.

The base material is preferably fibers like natural fibers, as e.g. cotton fibers and/or synthetic fibers, as e.g. thermoplastic fibers, and/or mineral fibers or a combination thereof. Beside fibres the base material can comprise further materials, e.g. in the form of flocks, liquids, powder, etc. For example a combination of scraps of a recycled material, like foam, shoddy etc, together with fibers is possible. Part of the base material can be binding material like binding fibers, powder or flakes, which are activated during the thermal treatment in the adjacent process step and/or in a later stage. Also the binding material with different activation mechanisms or processes or points can be used for instance with different melting temperatures. The material can than be preset during the forming and later for instance be combined with additional layers and finally moulded and laminated at another temperature activating a second binding material.

For the transport of the base material to the fiber feeding device state of the art fiber cleaning, mixing and dosing devices can be used. To ensure a good fiber distribution inside the cavity it is of advantage that the fiber bundles or clusters are opened up and that the material is fed substantially as single fibres or particles. The base material can be transported to the cavity using one or more transport rollers (feeding rollers) or using an air-laid method or a combination thereof. The fiber feed device is designed accordingly. By using transport rollers the base material, particularly the fibers, are laid down in the mould cavity, whereas in the air-laid method the base material, particularly the fibers, are blown into the mould cavity.

The base material feeding zone comprises at least one base material feeding device along the circumference and in the direction of rotation of the rotary drum. The use of multiple fiber feeding devices can be preferential if a layering of material is wanted or to obtain a certain material distribution. Also additional spraying devices for treatment of the base material for instance with anti flammability agents can be located over the width of the drum preferably in rotary direction downstream of at least the first base material feeding device.

The fiber feed device comprises most preferably a carding unit with a carding roller. The carding roller has the function of refining and moving the fibers from feeding rolls towards the product shaping area. A further function of the carding unit is to scrape the excess of fibers. The base material feeding stage of a fiber-feeding device preferably extends only along a relatively short peripheral distance in direction of rotation in order to reach a high fibre density in the cavity mould.

As the speed of rotation of the drum is constant and continuous it is preferred that the volume of base material fed can be regulated. Ways of regulating material feeding streams are known in the art.

Heating

At least one heating device is allocated to a subsequent second processing zone. In the second processing zone the shaped product is heated in order to consolidate the material. This can be a partial consolidation to obtain a stabilised preform, that keeps its shape during transport, or a full consolidation, to use the 3D shaped material directly as, or for, the final product, without further need for consolidation and or forming.

As a heating device different technologies can be used like heat radiation, for instance using infrared radiation, or convective heat transfer, for instance using a hot fluid, preferably hot air or steam. Also a combination of technologies can be applied subsequently or in parallel. The choice of heating technology is dependent on the base materials used and the shape and size of the final product. Contact heating is less preferred for a consolidation of the products emphasised as the time to heat up the material throughout is too long, this might damage the surface. However it might be an option if for instance to laminate to the visible surface of the base material while still in the cavity an additional covering layer.

All the heating devices are at least covering the largest width of the cavity in the perpendicular direction to the circumferential direction of the drum.

As the drum is continuous and constant moving in rotary direction the dwell time in the heating area is only dependent on the area that is covered by the heating device in circumferential direction. However the heating process of the product and therefore the amount of consolidation can be regulated by the temperature differential between the product and the heat load. Preferably the heat device can be regulated to form different zones with different heating temperatures in the rotary direction to control the process. For instance by using one heat source and but different pressure and/or airflows in different zones.

In the consolidating processing zone the heating device must be able to transfer enough heat into the base material in the cavity that might have different thicknesses, e.g. from 50 to 300 mm in order to carry out the consolidation or fixation, respectively, or the pre-fixation or pre-consolidation, respectively. Therefore, preferably hot blown air or steam is used to heat up the shaped product. However, if the air speed is too high, a deformation or even the destruction of the instable, shaped product can occur. The airflow is preferably directed in a radial direction towards the axis of rotation of the rotary conveyor, i.e. from the outside to the inside of the drum. The airflow is helped by the existing vacuum suction located inside the drum and that is already used for the filling of the cavity. Preferably the vacuum is set up such that the different processing zones do not interfere with each other.

Within the second processing zone containing the heating device one, two or even more than two heating or temperature zones, respectively with different temperatures can be provided. In these heating zones the temperature can preferably be set individually and independent from the other heating or temperature zones, respectively.

Due to the heat setting of the base material in the product forming cavity the base material is fixed in position this will prevent the disadvantageous of the prior art, in particularly the material will upon demoulding no longer be able to slide out of position therefore retaining the desired 3D shape. In addition, the edges obtained stay sharper and eventually holes are now possible in the technical designs of the new parts, without the necessity to cut them out again later. In a system without heat setting this was not possible as the fibers would slide upon unloading the mould, softening the part edges and filling small holes again with fiber material.

Demoulding

Downstream of the consolidating process zone the consolidated product can be demoulded in a subsequent processing zone. The 3D shaped, consolidated product is removed from the product-forming cavity. In the simplest form the product can be transferred to a table, or other form of stationary device that is used for collecting the consolidated products, or it is in the form of a conveying device for transport of the consolidated product for further processing, for instance a conveyer belt or robotic transport or it is a combination depending on the actual product produced.

Cooling

In a further development of the invention the product-shaping device further contains an additional zone before the demoulding, to which a cooling device is allocated. The cooling zone is arranged along the circumference and in the direction of rotation of the rotary conveyor between the consolidating zone and the demoulding zone. In the cooling processing zone the previously heated shaped product is cooled as a further step of the initial solidification. The fiber feed device, the at least one heating device, the eventually cooling device and the transfer device and hence the corresponding processing zones are stationary arranged alongside the peripheral surface of the rotary conveyor during the production of the consolidated 3D product. Optionally the cooling device in the cooling zone can be replaced with an additional heating device for optimal flexibility in the use of the machinery. The preferred solution for cooling the product would be the use of a fluid stream preferably in the form of airflow, either at ambient temperature or cooled to optimise the cooling process. The cooling of the part can also be helped by the use of negative pressure in the product-forming cavity.

Other Processes

In addition to the filling of the cavity, the consolidation of the material and the demoulding eventually an additional process step might be integrated in the machine and process according to the invention. Either before or during the heating and/or cooling process step the base material might be compacted. For instance by increasing the pressure during the heating and/or cooling phase, or just before starting the consolidation but after the fiber feeding. For instance with a pressure roller or by using an air flow or increasing the negative pressure in at least the part of the cavity that is filled with the base material.

Method of Producing

For carrying out the method of manufacturing a 3D shaped consolidated product containing base material an apparatus as described above is used. The method comprises steps of:

While the invention has been described in present preferred embodiments of the invention, it is distinctly understood that the invention is not limited thereto, but may be otherwise variously embodied and practised within the scope of the claims.

BRIEF DESCRIPTION OF DRAWINGS

FIG. 1 shows the device according to the invention. The core of the device forms a rotary drum 3 with at least one cavity 4. The surface is at least partially pervious at the areas of the cavity forming the shape of the wanted product. In the cavity at the side facing the fibre stream 1 the fibers are collected until the cavity is full. Preferably a device for elimination of excess material is given, before the consolidation zone B. A take-off roller or a scraping knife, or alternative solutions known in the art can be used for this purpose. Another solution is a combination with the feeding device.

Figure 1:
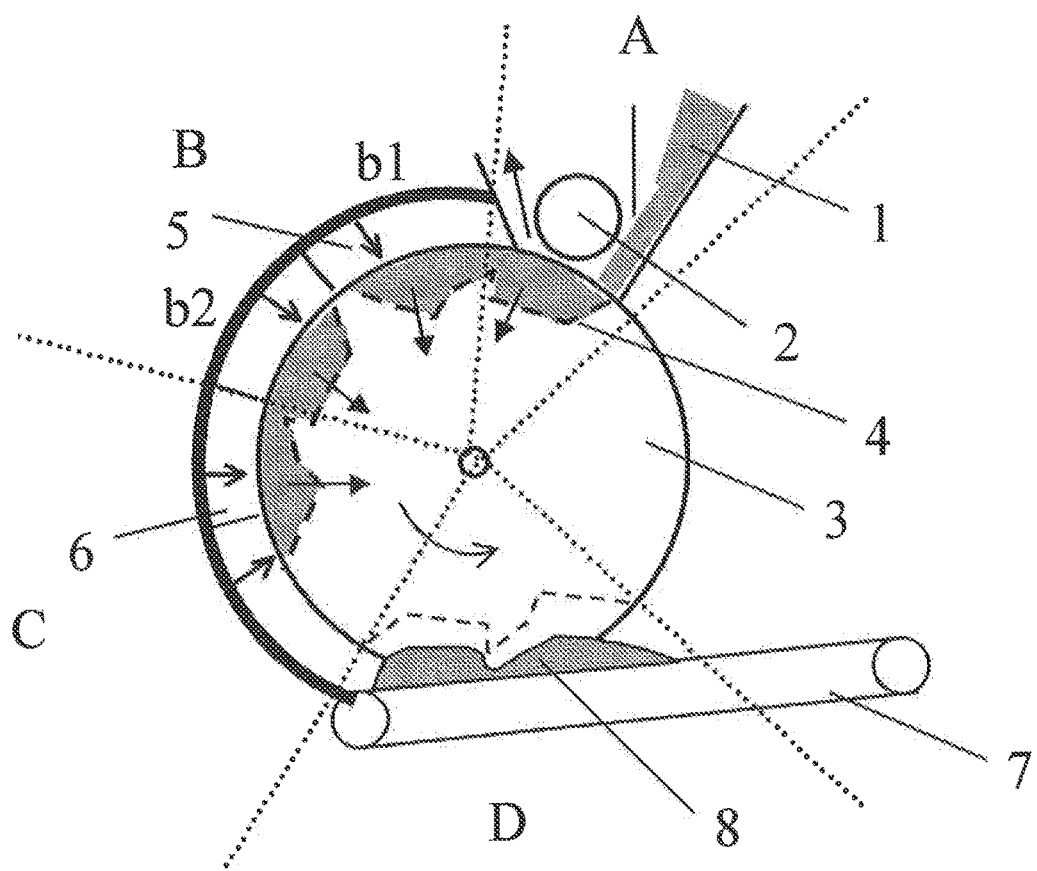
FIG. 1 shows a schematic drawing of the device according to the invention.

Inside the drum a device or means for producing a negative pressure in the cavity where the product is formed is located. This can be for instance a vacuum device or connections to an external vacuum device. The connections to the vacuum device can be built independently for the different processing zones. Airstreams through the cavity are shown with arrows.

Due to the rotary movement the cavities will pass different processing steps or zones. These different processing steps or zones are as follows:

A. Feeding of the base material into the cavity;
B. Consolidation of the base material collected in the cavity;
C. Eventually cooling of the consolidated material in the cavity;
D. Demoulding of the 3D shaped consolidated material from the cavity.

The device 2 in zone A is an example of such base material feeding device that can be used according to the invention. The fibrous stream is fed in the cavity using a carding roll which at the same time also removes surplus material as disclosed in WO 2007/134812.

The filled cavities 4 are passing in zone B at least one consolidating device 5 for instance a heating device for thermal treatment of the cavity filled with base material to heat-set the material. In the example two thermal zones are used, b1 and b2, whereby the temperature Tb1 is different from Tb2. As the transfer of heat is dependent on the material properties as well as the temperature of the material, it might be necessary to keep a certain delta between the temperature of the fluid used and the temperature of the product. In particularly care has to be taken that the material is not damaged—overheated and burnt—on the surface, as this can have a negative effect on the product quality. The use of different temperature zones has the advantage that the amount of heat transferred can be adjusted more optimally. An example of a temperature zoning can be a heat up zone and a zone where the temperature is kept constant at a higher level. The consolidation of the base material is dependent on the overall heat that is put into the material. Preferably a hot air flow, the temperature of the hot air and eventually the pressure in the treatment zone can be adjusted.

Downstream of the consolidating process zone the consolidated product can be demoulded in a subsequent processing zone D. The 3D shaped, consolidated product 8 is removed from the product-forming cavity. In the simplest form the product can be transferred to a table, or other form of stationary device that is used for collecting the consolidated products, or it is in the form of a conveying device for transport of the consolidated product for further processing, for instance a conveyer belt 7 or robotic transport or it is a combination depending on the actual product produced.

Figure 2:
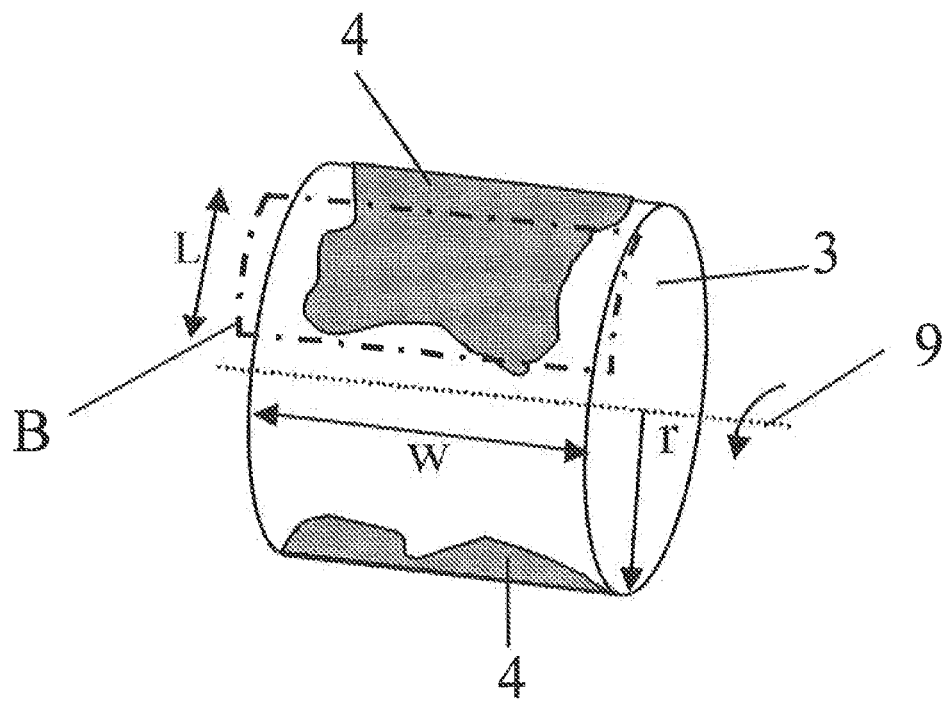
FIG. 2 shows a schematic drawing of the device according to the invention from a different angle.

FIG. 2 shows the rotary drum 3 with 2 cavities 4, which rotates around an axis of rotation 9 and has a certain width w and a certain radius r. With a dashed line the consolidation zone B is given that extends at least over the largest width of the cavity, but preferably over the complete width of the drum W. The dwell time is dependent on the rotary speed of the drum, as also the feeding of the cavity, the cooling and the lay down is dependent on this factor, therefore the dwell time can only be regulated with the length L of the circumferential area that is opposite the consolidating device as shown in the dashed line.

For instance the cooling area 6 in the cooling zone C in FIG. 1 might be adjustable to extend the consolidating area.

Figure 3:
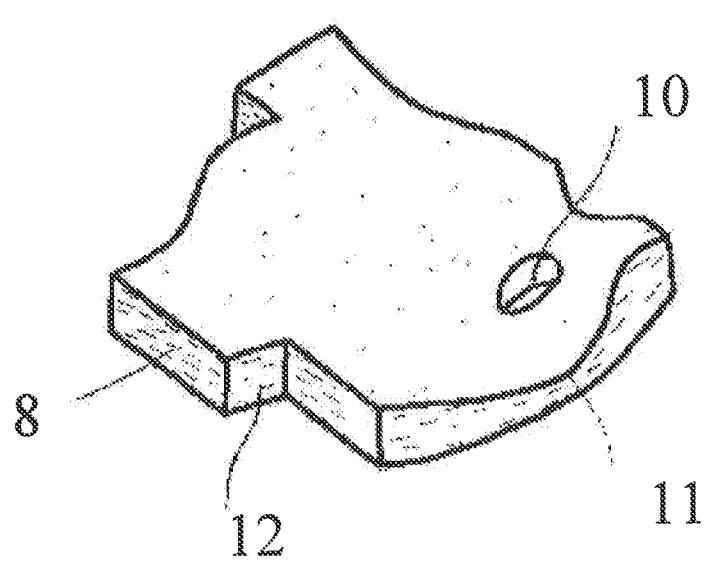
FIG. 3 shows an example of a consolidated product preform or end product.

FIG. 3 shows an example of a 3D shaped consolidated product 8 made of base material for instance fibres produced according to the invention, with technical design features, that includes a re-entrant portion 12, a hole 10 and an area with a thickness reduction 11.

The invention claimed is:

1. A device for producing a three-dimensional shaped consolidated fibrous product from a fibrous base material, comprising:
    a rotary drum, defined as a rotary conveyor with a peripheral surface extending in a circumferential direction, with at least one product shaping area in the form of at least one cavity being formed on said peripheral surface, the peripheral surface is pervious to air at least in the product shaping area;
    at least one fiber feed device to feed the fibrous base material into the at least one cavity, the fiber feed device arranged to feed the fibrous base material substantially as single fibers or particles;
    a vacuum device designed to generate a negative pressure at least in the at least one cavity, thereby generating suction directed towards an interior of the rotary conveyor;
    at least one consolidating device that comprises at least one heating device configured to provide thermal energy to the at least one cavity and fibrous base material contained in the at least one cavity, the at least one consolidating device being located downstream of the fiber feed device and heat-sets the fibrous base material by subjecting it to a consolidating treatment whereby the fibers in the fibrous base material in the cavity are at least partially adhered; and
    wherein the rotary drum is defined by a first zone and a second zone, and wherein the at least one heating device is configured to provide a heat of a first temperature to the first zone and heat of a second temperature to the second zone.

2. The device according to claim 1, wherein the thermal energy is delivered to the fibrous base material by at least one of heat radiation and convective heat transfer, and wherein the heating device does not provide contact heating.

3. The device according to claim 1, wherein the at least one consolidation device defines a consolidating zone that is divided into different treatment zones in direction of rotation.

4. The device according to claim 3, further comprising a demolding device, located after the consolidating zone, for demolding and transferring the consolidated fibrous product to a stationary area.

5. The device according to claim 4, further comprising a cooling device located between the consolidating zone and the demolding zone for providing a cooling zone that cools the consolidated fibrous product, the cooling device generating airflow that has a temperature less than that of ambient air.

6. The device according to claim 5, wherein the cooling zone comprises at least one cooling device that generates an airflow that is directed towards an axis of rotation of the rotary drum.

7. The device according to claim 4, wherein the fiber feed device, the at least one consolidating device, and the demolding device are all stationary located around the peripheral surface of the rotary drum, whereby the fiber feed device, the at least one consolidating device, and the demolding device cover at least the maximum width of the cavity.

8. The device according to claim 1, wherein the vacuum device is regulated to change the negative pressure in the cavity depending on the location of the cavity during rotation.

9. The device according to claim 3, wherein the consolidating zone is divided into different treatment zones with different air flows.

10. The device according to claim 3, wherein after the consolidating zone, a consolidated product is demolded and transferred to a conveying device.

11. The device according to claim 1, wherein the fiber feed device comprises one or more transport rollers.

12. The device according to claim 1, wherein the fiber feed device uses an air-laid method.

13. The device according to claim 1, wherein the fiber feed device is a carding roller.

14. The device according to claim 1, wherein the negative pressure is comprised of a first negative pressure and a second negative pressure, the first negative pressure and the second negative pressure being different.

15. The device according to claim 1, wherein the vacuum device is configured to provide a first negative pressure to the first zone and a second negative pressure to the second zone, and wherein the consolidating device comprises the at least one heating device.

16. The device according to claim 1, wherein the at least one cavity is lined with an air pervious material selected from a group consisting of metal mesh and wire cloth.

17. The device according to claim 16, wherein the air pervious material has a first portion that provides a first air resistance and a second portion that provides a second air resistance.

18. A device for producing a three-dimensional shaped consolidated fibrous product from a fibrous base material, comprising:
    a rotary drum, defined as a rotary conveyor with a peripheral surface extending in a circumferential direction, with at least one product shaping area in the form of at least one cavity being formed on said peripheral surface, the peripheral surface is pervious to air at least in the product shaping area;
    at least one fiber feed device to feed the fibrous base material into the at least one cavity, the fiber feed device arranged to feed the fibrous base material substantially as single fibers or particles;
    a vacuum device designed to generate a negative pressure at least in the at least one cavity, thereby generating suction directed towards an interior of the rotary conveyor;
    at least one consolidating device that comprises at least one heating device configured to provide thermal energy to the at least one cavity and fibrous base material contained in the at least one cavity, the at least one consolidating device being located downstream of the fiber feed device and heat-sets the fibrous base material by subjecting it to a consolidating treatment whereby the fibers in the fibrous base material in the cavity are at least partially adhered; and
    wherein the at least one consolidating device defines a consolidating zone that is divided into a first treatment zone that exposes the fibrous base material to at least a first temperature and a second treatment zone that exposes the fibrous base material from the first treatment zone to at least one of a second temperature.

* * * * *